(12) United States Patent
Searfoss et al.

(10) Patent No.: US 10,603,488 B2
(45) Date of Patent: Mar. 31, 2020

(54) IMPLANTABLE MEDICAL DEVICES HAVING DIAMAGNETIC CONDUCTORS AND CONTACTS

(71) Applicant: Oscor Inc., Palm Harbor, FL (US)

(72) Inventors: Timothy Searfoss, New Port Richey, FL (US); Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 168 days.

(21) Appl. No.: 15/894,474

(22) Filed: Feb. 12, 2018

(65) Prior Publication Data

US 2018/0229031 A1    Aug. 16, 2018

Related U.S. Application Data

(60) Provisional application No. 62/457,372, filed on Feb. 10, 2017.

(51) Int. Cl.
| | |
|---|---|
| *A61N 1/08* | (2006.01) |
| *A61L 31/02* | (2006.01) |
| *A61N 1/05* | (2006.01) |
| *B29L 31/00* | (2006.01) |
| *B29C 65/66* | (2006.01) |

(52) U.S. Cl.
CPC ............ *A61N 1/086* (2017.08); *A61L 31/022* (2013.01); *A61L 31/024* (2013.01); *A61N 1/056* (2013.01); *B29C 65/66* (2013.01); *B29L 2031/7534* (2013.01)

(58) Field of Classification Search
CPC . A61N 1/086; A61N 1/056; B29L 2031/7534; A61L 31/024; A61L 31/022
See application file for complete search history.

(56) References Cited

U.S. PATENT DOCUMENTS

| | | | |
|---|---|---|---|
| 6,494,860 | B2 | 12/2002 | Rocamora et al. |
| 6,671,562 | B2 | 12/2003 | Osypka et al. |
| 6,684,109 | B1 | 1/2004 | Osypka |
| 6,711,443 | B2 | 3/2004 | Osypka |
| 6,738,674 | B2 | 5/2004 | Osypka |
| 6,892,087 | B2 | 5/2005 | Osypka |
| 6,978,185 | B2 | 12/2005 | Osypka |
| 7,120,504 | B2 | 10/2006 | Osypka |
| 7,128,600 | B2 | 10/2006 | Osypka |
| 7,151,965 | B2 | 12/2006 | Osypka |
| 7,158,837 | B2 | 1/2007 | Osypka et al. |
| 7,187,980 | B2 | 3/2007 | Osypka et al. |

(Continued)

*Primary Examiner* — Catherine M Voorhees
(74) *Attorney, Agent, or Firm* — Locke Lord LLP; Scott D. Wofsy

(57) ABSTRACT

An implantable medical device includes an elongated tubular body having opposed proximal and distal end portions and defining a longitudinal axis. The elongated tubular body includes an interior lumen extending therethrough. A plurality of axially spaced apart electrode rings are operatively associated with the distal end portion of the tubular body. The electrode rings are formed from at least one of bismuth or pyrolytic graphite. A plurality of electrical conductors extend through the interior lumen of the tubular body. Each of the electrical conductors is operatively associated with a respective one of the plurality of electrode rings. The electrical conductors are formed from at least one of bismuth or carbon fiber.

10 Claims, 5 Drawing Sheets

(56) References Cited

U.S. PATENT DOCUMENTS

| | | | |
|---|---|---|---|
| 7,192,433 B2 | 3/2007 | Osypka et al. | |
| 7,197,361 B2 | 3/2007 | van den Nieuwenhof et al. | |
| 7,241,180 B1 * | 7/2007 | Rentas Torres | A61N 1/05 439/668 |
| 7,270,568 B2 | 9/2007 | Osypka | |
| 7,421,295 B2 | 9/2008 | Osypka | |
| 7,467,017 B2 | 12/2008 | Osypka | |
| 7,904,161 B2 | 3/2011 | Osypka | |
| 8,137,317 B2 | 3/2012 | Osypka | |
| 8,224,463 B2 | 7/2012 | Worley | |
| 8,244,376 B2 | 8/2012 | Worley | |
| 8,262,671 B2 | 9/2012 | Osypka | |
| 8,649,878 B2 * | 2/2014 | Swoyer | A61N 1/0529 607/116 |
| 9,061,120 B2 | 6/2015 | Osypka et al. | |
| 9,295,828 B2 | 3/2016 | Halperin et al. | |
| 9,463,317 B2 | 10/2016 | Conroy et al. | |
| 9,492,651 B2 | 11/2016 | Bottomley et al. | |
| 9,520,213 B2 | 12/2016 | Koziol et al. | |
| 2007/0079511 A1 | 4/2007 | Osypka | |
| 2007/0219547 A1 | 9/2007 | Osypka | |
| 2007/0299493 A1 | 12/2007 | Osypka | |
| 2008/0311772 A1 | 12/2008 | Osypka | |
| 2010/0137956 A1 | 6/2010 | Osypka | |
| 2010/0305509 A1 | 12/2010 | Osypka et al. | |
| 2010/0312190 A1 | 12/2010 | Searfoss et al. | |
| 2011/0264162 A1 | 10/2011 | Osypka et al. | |
| 2012/0253445 A1 | 10/2012 | Osypka | |
| 2012/0265281 A1 | 10/2012 | Osypka | |
| 2013/0030512 A1 | 1/2013 | McCready et al. | |
| 2013/0072956 A1 | 3/2013 | Searfoss et al. | |
| 2013/0116765 A1 | 5/2013 | Osypka et al. | |
| 2014/0050861 A1 | 2/2014 | Vaidyanathan et al. | |
| 2014/0072872 A1 * | 3/2014 | Hodgkinson | H01M 6/04 429/213 |
| 2015/0045696 A1 | 2/2015 | Osypka | |
| 2015/0057610 A1 | 2/2015 | Osypka et al. | |
| 2015/0057655 A1 | 2/2015 | Osypka | |
| 2015/0105721 A1 | 4/2015 | Osypka et al. | |
| 2017/0080215 A1 | 3/2017 | Osypka | |
| 2017/0189669 A1 * | 7/2017 | Kamarajugadda | A61N 1/05 |

* cited by examiner

Fig. 6
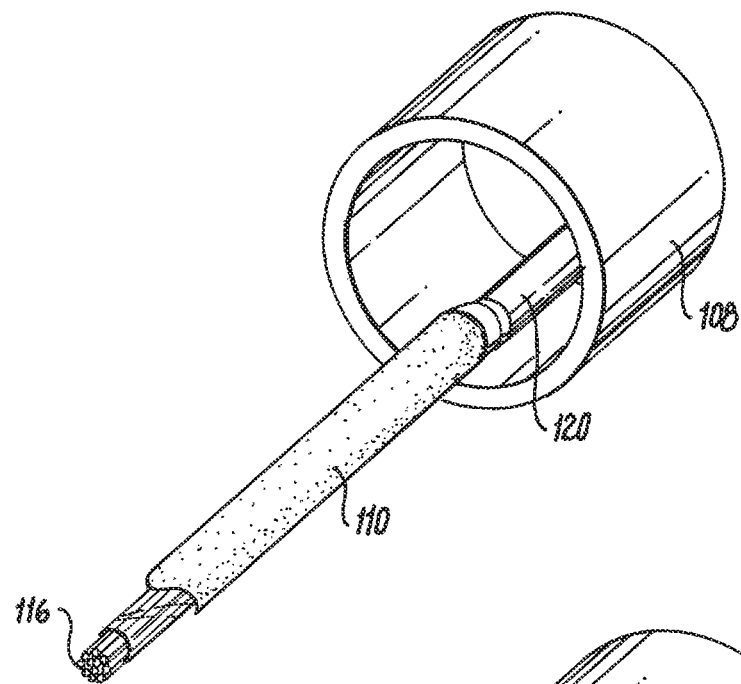
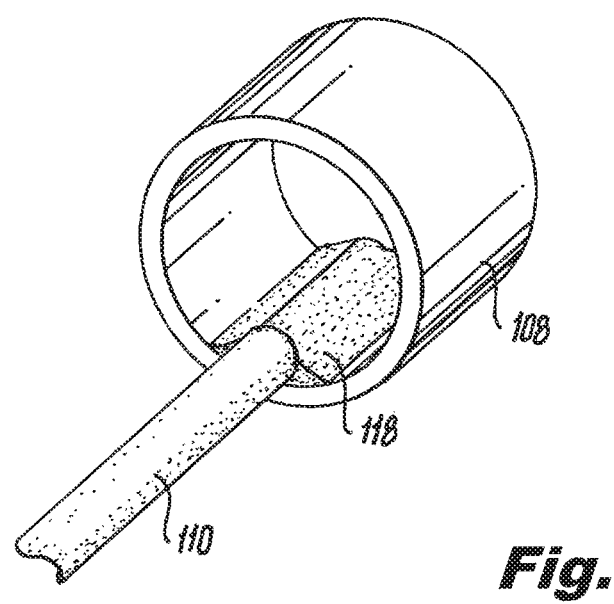
Fig. 7

IMPLANTABLE MEDICAL DEVICES HAVING DIAMAGNETIC CONDUCTORS AND CONTACTS

CROSS-REFERENCE TO RELATED APPLICATION

This application claims the benefit of priority to U.S. Provisional Patent Application No. 62/457,372, filed Feb. 10, 2017, which is incorporated by reference herein in its entirety.

BACKGROUND OF THE INVENTION

1. Field of the Invention

The subject disclosure relates to implantable medical devices, and more particularly, to implantable cardiac leads that include conductors and contacts made from diamagnetic materials to reduce electromagnetic interference and induction heating.

2. Description of Related Art

An electromagnetic interference environment in very close proximity to the human body may create difficulty for implantable medical devices to perform well without compromising the safety and performance of the electromagnetic interference environment.

There is a wide variety of magnetic interference that can be in close proximity to the body (in the pocket) with the use of portable transmitting and receiving electronics, (Cell Phone, Tablet, Laptop) and in some cases multiple combined emissions and their harmonics. These, and other emissions, e.g. through WIFI, metal detectors, and the like, can influence the millivolt level operation signals of the implantable medical devices that can be life critical. For example, if the induced electromagnetic radiation induces a signal out of phase with the normal heart signals, this can cause the signal generator to not operate properly. The different frequency spectrum of these signals makes the design of immune to electrical magnetic interference implantable devices a complex endeavor.

The greatest electromagnetic interference is currently during a Magnetic Resonance Imaging (MRI) session or a Magnetic Resonance Tomography (MRT) imaging session. Current approaches to diminish the electromagnetic induction heating and alteration of the low voltage normal operation signals has been to design ICR (Induction Capacitance Resistance) self-resonant notch filter characteristics by the use of inductance, multi turn coiling of the conductors along with the tuning of the insulation characteristics (capacitance) so that the implanted electrical conductors have a high impedance at a particular frequency.

Series connection of multiple tuned induction capacitive aspects are also used to self-resonate at the two main MRI frequencies of 1.5 Tesla 64 MHz and 3.0 Tesla 128 MHz. This is described in U.S. Pat. Nos. 9,295,828 and 9,492,651. Another method is the use of braid over the length of the conductors where the induction and capacitance of the braid is also carefully tuned to have high impedance at the particular resonance frequency, as described in U.S. Pat. No. 9,463,317, and thereby shield the inner conductors from the electromagnetic induction.

Another method is to alter the surface of the conductors themselves with nanometer and micron size particles of different conductive metals disrupting the flow of the electromagnetic induction into the conductor by creating micro islands of swirling magnetic fields on the surface that do not add to the conductor itself. This is described in U.S. Patent Publication No. 2014/0050861 A1.

These methods are capable of meeting acceptable safety margins. However, it is desired to achieve improved integrity and reliability of the low voltage signals that are in an implanted heart lead, circuitry, defibrillation conductors, circuitry, and many other neuro-stimulation electrical conductors, electrodes, and circuitry. Conventional methods and systems have generally been considered satisfactory for their intended purpose. However, there is still a need in the art for devices that reduce the electromagnetic induction and interference of implantable electrical devices, conductors and electrodes. This disclosure provides a solution for these needs.

SUMMARY OF THE INVENTION

An implantable medical device includes an elongated tubular body having opposed proximal and distal end portions and defining a longitudinal axis. The elongated tubular body includes an interior lumen extending therethrough. A plurality of axially spaced apart electrode rings are operatively associated with the distal end portion of the tubular body. The electrode rings are formed from at least one of bismuth or pyrolytic graphite. A plurality of electrical conductors extend through the interior lumen of the tubular body. Each of the electrical conductors is operatively associated with a respective one of the plurality of electrode rings. The electrical conductors are formed from at least one of bismuth or carbon fiber.

The device can include an inner dielectric support structure extending through the interior lumen of the elongated tubular body for supporting the plurality of electrical conductors. The inner dielectric support structure can be positioned radially inward from the electrode rings. A dielectric insulator ring can be positioned between axially adjacent pairs of spaced apart electrode rings. The electrode rings can be co-axial with one another. Each of the electrical conductors can include an axially extending bundle of fibers that is jacketed by a dielectric insulation material. Each of the electrical conductors can include a conductive distal tip electrically connected to a respective one of the plurality of electrode rings.

In accordance with some embodiments, a composite adhesive material is used to secure each electrical conductor to a respective one of the plurality of electrode rings. The composite adhesive material can include a micro-particle concentration of carbon fiber and/or pyrolytic graphite powders. A connector assembly can be operatively associated with the proximal end portion of the tubular body for connecting the implantable medical device to an implantable stimulation device. The carbon fiber can be a nano-tube carbon fiber. The electrical conductors can be formed from a mixture of carbon fiber powder, pyrolytic graphite powder, and an adhesive. The adhesive can include at least one of a two-part epoxy, cyanoacrylate, or ultra-violet cured adhesives.

In accordance with another aspect, a method for assembling an implantable medical device having electrical conductors includes providing an elongated tubular body having opposed proximal and distal end portions. The elongated tubular body defines a longitudinal axis and including an interior lumen extending therethrough. The method includes heat-shrinking a heat-shrink material over an axially extending bundle of fibers to compress the heat shrink material around the axially extending bundle of fibers. The method includes jacketing a dielectric insulating material around the axially extending bundle of fibers to form an electrical conductor. The method includes positioning the electrical conductor within the interior lumen of the elongated tubular body.

Jacketing the dielectric insulating material around the axially extending bundle of fibers can include applying heat to the dielectric insulating material.

In some embodiments, heat-shrinking the heat-shrink material over an axially extending bundle of fibers is before jacketing the dielectric insulating material around the axially extending bundle of fibers.

In some embodiments, jacketing the dielectric insulating material around the axially extending bundle of fibers is before heat-shrinking the heat-shrink material over the axially extending bundle of fibers. Heat-shrinking the heat-shrink material over the axially extending bundle of fibers can include heat-shrinking the heat-shrink material over the dielectric insulating material and the axially extending bundle of fibers at the same time with the same heat-shrink material. The method can include applying heat to the dielectric insulating material after heat-shrinking the heat-shrink material over the dielectric insulating material and the axially extending bundle of fibers. The method can include removing heat-shrink material after applying heat to the dielectric insulating material.

These and other features of the subject invention and the manner in which it is manufactured, assembled and employed will become more readily apparent to those having ordinary skill in the art from the following enabling description of the preferred embodiments of the subject invention taken in conjunction with the several drawings described below.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 6 is a schematic perspective view of a portion of an electrical conductor of the implantable medical device of FIG. 1, showing a conductive distal tip of the electrical conductor electrically connected to one of the plurality of electrode rings;

FIG. 7 is a schematic perspective view of a portion of an electrical conductor of the implantable medical device of FIG. 1, showing a conductive distal tip of the electrical conductor coupled to the electrode rings with an adhesive coating;

DETAILED DESCRIPTION OF THE PREFERRED EMBODIMENTS

Figure 1:
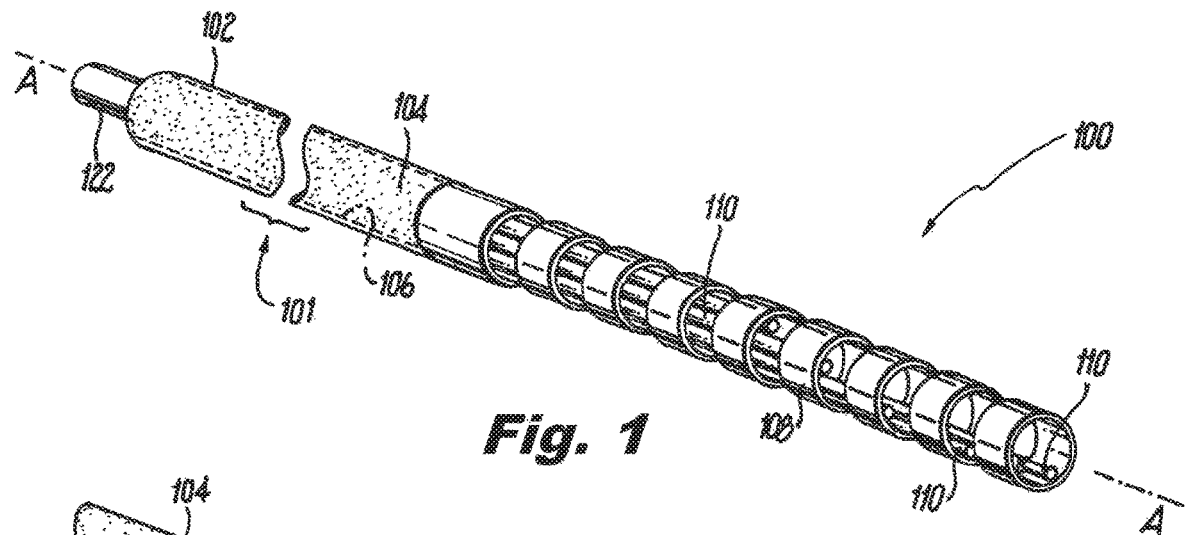
FIG. 1 is a schematic perspective view of a portion of an exemplary embodiment of an implantable medical device constructed in accordance with the present disclosure, showing an elongated tubular body with plurality of electrical conductors disposed within the elongated tubular body.

Reference will now be made to the drawings wherein like reference numerals identify similar structural features or aspects of the subject disclosure. For purposes of explanation and illustration, and not limitation, a partial view of an exemplary embodiment of an implantable medical device in accordance with the disclosure is shown in FIG. 1 and is designated generally by reference character 100. Other embodiments of an implantable medical devices, and systems and methods in accordance with the disclosure, or aspects thereof, are provided in FIGS. 2-9, as will be described. The devices, systems and methods described herein use diamagnetic materials that when exposed to the influence of an external H-field (external magnetic induction field) create an opposite field due to the atomic structure of their valence electron configuration. The use of these materials in the implanted electrical devices reduces the effects of electromagnetic induction, heating, and noise, as compared with traditional materials, due to their intrinsic properties. For example, in the case of an electro-magnetic-pulse event the diamagnetic materials used in the implantable devices described below will perform without harm to the patient, as compared to the current implantable lead technology that would result in an excessive high voltage pulse to the tissue, with the potential to be fatal.

As shown in FIG. 1, an implantable medical device 100 includes an elongated tubular body 101. Elongated tubular body 101 includes a proximal end portion 102 and an opposing distal end portion 104. Elongated tubular body 101 defines a longitudinal axis A. Elongated tubular body 101 includes an interior lumen 106 extending therethrough. A connector assembly 122 is operatively associated with the proximal end portion 102 of the tubular body 101 for connecting the implantable medical device 100 to an implantable stimulation device (not shown), pulse generator or the like, as disclosed for example in commonly assigned U.S. Patent Application Publication No. 2012/0253445, the disclosure of which is herein incorporated by reference in its entirety.

Figure 2:
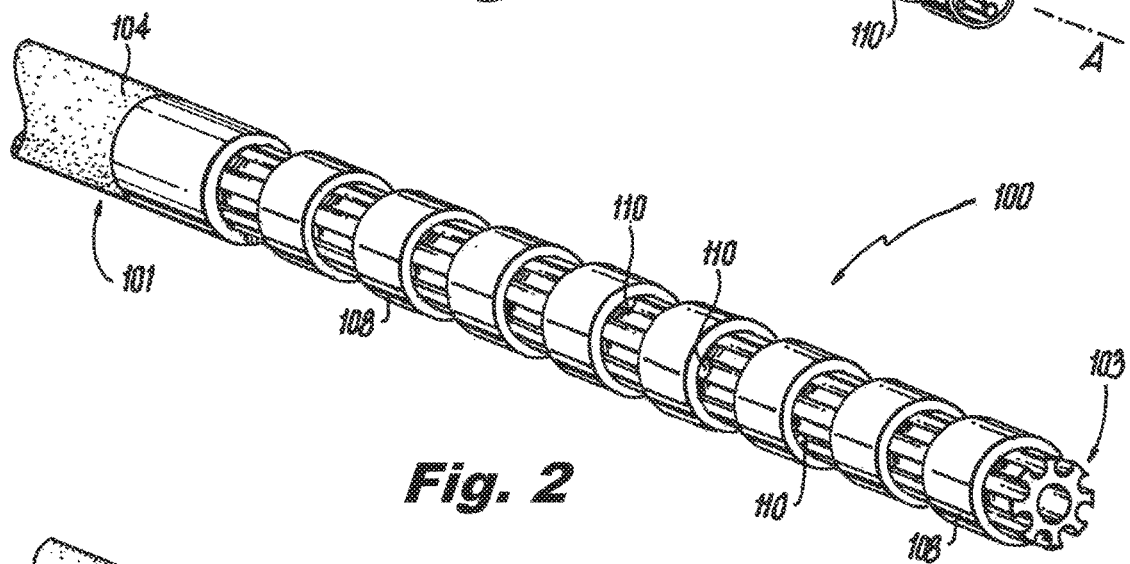
FIG. 2 is a schematic perspective view of the distal end portion of the implantable medical device of FIG. 1, showing the electrical conductors being supported via an inner dielectric support structure.
Figure 3:
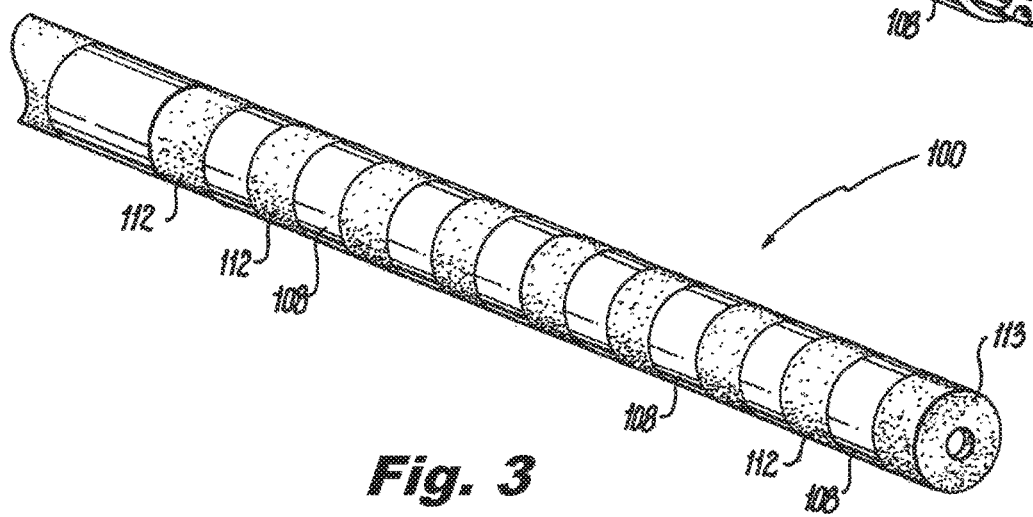
FIG. 3 is a schematic perspective view of the distal end portion of the implantable medical device of FIG. 1, showing dielectric insulator rings positioned between axially adjacent spaced apart electrode rings.

With continued reference to FIGS. 1 and 2, a plurality of electrode rings 108 are operatively associated with the distal end portion of the tubular body 101. Electrode rings 108 are spaced apart from one another in an axial direction, e.g. along the longitudinal axis. Electrical conductors 110 extend through the interior lumen 106 of tubular body 101. Each electrical conductor 110 is operatively associated with one of electrode rings 108. As shown in FIG. 2, device 100 includes an inner dielectric support structure 103 extending through interior lumen 106 of elongated tubular body 101 for supporting electrical conductors 110. As shown in FIG. 3, a dielectric insulator ring 112 is positioned between axially adjacent spaced apart electrode rings 108. Device 100 includes a dielectric insulated tip 113.

Figure 4A:
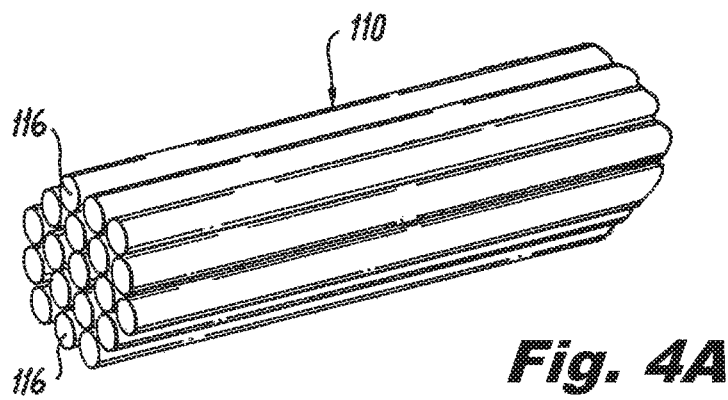
FIG. 4A is a schematic perspective view of a portion of an electrical conductor of the implantable medical device of FIG. 1, showing a bundle of fibers that form the electrical conductor.
Figure 4B:
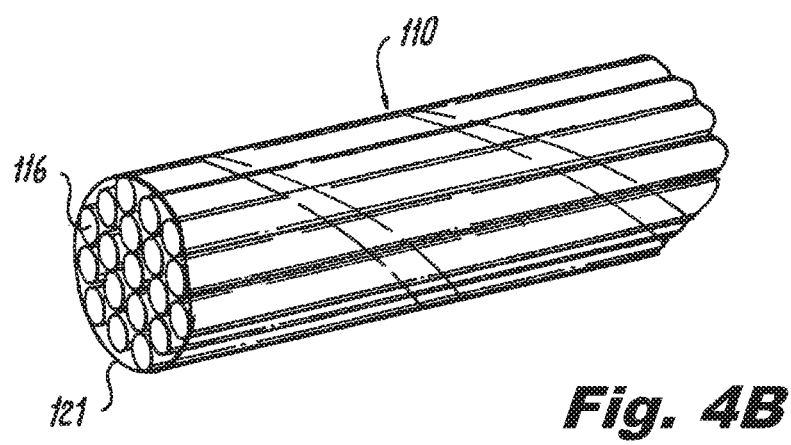
FIG. 4B is a schematic perspective view of a portion of an electrical conductor of the implantable medical device of FIG. 1, showing the bundle of fibers from FIG. 4A with a heat shrink material positioned around an outer perimeter of the bundle.
Figure 5:
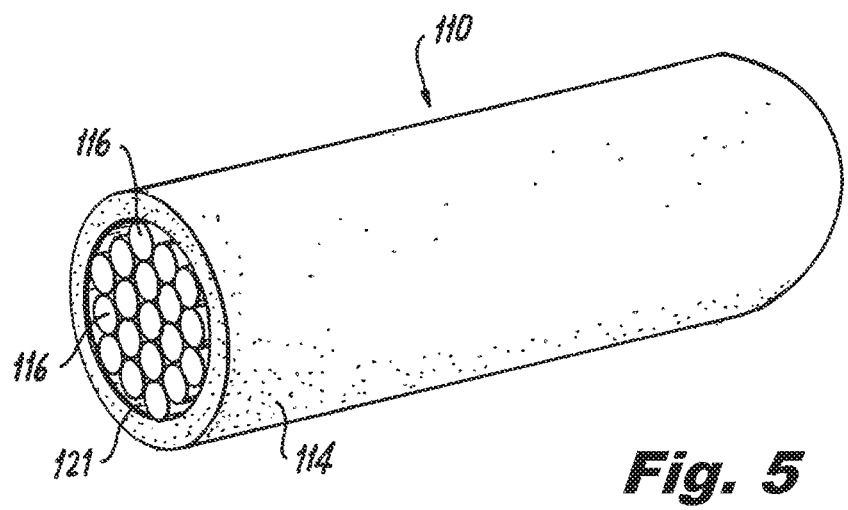
FIG. 5 is a schematic perspective view of a portion of an electrical conductor of the implantable medical device of FIG. 1, showing a portion of the bundle of fibers jacketed with a dielectric insulation material.

With reference now to FIGS. 4A-5, electrode rings 108 are formed from bismuth, pyrolytic graphite and/or highly ordered pyrolytic graphite (HOPG). Each electrical conductor 110 includes an axially extending bundle of fibers 116 that is jacketed by a dielectric insulation material 114. Fibers 116 extend along the longitudinal axis A. Fibers 116 contain bismuth, carbon fiber, and/or carbon nano-tube fibers. Fibers 116 are interchangeably referred to hereinafter as bismuth fibers/wires, carbon fibers and/or nano-tube fibers. Pyrolytic graphite is a type of synthetic graphite and HOPG is a highly pure version of pyrolytic graphite. Pyrolytic Graphite and HOPG are very diamagnetic materials, such as is currently utilized in permanently implanted heart valves. The electrical, magnetic, thermal, and strength properties of pyrolytic graphite and HOPG, discussed in more detail below, are superior to the materials of the current art. For example, no shielding would be required to conform to the demanding MRI, MRT requirements.

Bismuth has the highest diamagnetic magnetic susceptibility of all of the elements. When exposed to a permanent magnet it is mildly repelled, but due to the small volume of material used in implantable device 100, it is well within the MRI compatibility displacement characteristics. Bismuth is known to be biocompatible and is also ingested and is an ingredient in a popular "Pepto-Bismol" over the counter product. Forming electrical conductors 110 and/or electrode rings 108 out of bismuth reduces the electrical magnetic induction and induced noise during an MRI, MRT, or other electromagnetic induction exposure. It is contemplated that bismuth can be laser welded, resistive welded, as traditional platinum iridium electrodes are currently. Bismuth can be jacketed over, or extruded with insulation. It is contemplated that the low melting point of bismuth may limit the extrusion to using extrusion materials having a lower melt temperature.

In embodiments where bismuth wires/fibers 116 form the bismuth conductor 110, for example, fibers 116 are insulated by extruding high dielectric insulation material 114 over a bundle of bismuth fibers 116, or by slipping a pre-extruded dielectric insulation material over the bismuth conductor wires 116 and heating in a reflow process where time and temperature can be controlled. In some embodiments, as shown in FIGS. 4B-5, a heat shrink material 121 can be placed over the bundle of fibers 116, covered with dielectric insulation, and then heated. In another embodiment, as described in more detail below, heat shrink material similar to 121 can be placed around the outer circumference of dielectric insulation material 114. By using the latter process, the heat shrink will collapse the dielectric insulation 114 over the bismuth wire or wires during the heating process. The heat shrink can then be removed once cooled down to room temperatures, resulting in final conductor 110, as shown in FIG. 5, except without the heat shrink material 121 that is shown around the bundle of fibers 116. This process is described in more detail below in the context of FIG. 9 below.

It is contemplated that bismuth conductors 110 and electrode rings 108 can be combined with the prior stated current art of notch filtering, self-resonance, braid shielding, and surface alteration methods to further customize the performance of the devices. The use of bismuth provides lower induced noise, and lower electromagnetic heating, as compared with traditional materials, providing a safer product for the patient. The use of bismuth as a material for the conductors 110 and electrode rings 108 can also be utilized in the construction of the electronic signal monitoring and generator components such as the header conductive rings, and conductors. As was noted above, in some embodiments, electrode rings 108 are formed from pyrolytic graphite and/or HOPG. Similar to bismuth, pyrolytic graphite and HOPG are also biocompatible. The diamagnetic magnetic susceptibility characteristics of pyrolytic graphite and HOPG make it an ideal material for the electrode rings 108 or other electrodes of implantable heart leads, and other neuro-stimulation devices. The electrical conductivity performance of pyrolytic graphite and HOPG are also better than that of traditional electrode materials. The diamagnetic properties of the pyrolytic graphite and HOPG tend to reduce the electromagnetic induction during MRI and MRT procedures, as compared with traditional electrodes, and also reduce the electromagnetic induction of other electromagnetic noise in the environment. The construction of an implanted stimulation device, similar to the stimulation device described above in the context of commonly assigned U.S. Patent Application Publication No. 2012/0253445, can also benefit from the use of pyrolytic graphite and/or HOPG. For example, the electrodes in the header of an implanted stimulation device can be formed from pyrolytic graphite and/or HOPG. It is also contemplated that the construction of the casing of an implanted stimulation device can also be made of pyrolytic graphite and/or HOPG which is more conductive than the current stainless steels and other materials utilized in this construction. This can prevent the implanted stimulation device from heating during the MRI or MRT procedures.

One challenge with using pyrolytic graphite and HOPG for electrode rings 108 has been ensuring reliable connection of the pyrolytic graphite and HOPG electrode rings 108 to electrical conductors 110, as pyrolytic graphite and HOPG do not typically solder, laser weld, or resistive weld well. However, embodiments of the present invention provide for adhesive materials and methods of adhering conductors 110 to electrode rings 108 that overcome the challenges previously presented.

Using carbon fiber and/or nano-tube carbon fibers 116 to form conductors 110 offers advantages for the construction of implantable heart leads, and neuro-stimulation devices as carbon fiber conductors (whether nano-tube, or otherwise) have very low resistance. Carbon fiber and nano-tube carbon (generically referred to hereinafter as "carbon fiber") are very flexible and do not require the multi-thread coiling currently utilized in the manufacture of heart leads. Carbon fiber is also very durable and can flex millions of cycles without degradation of the performance. Conductors 110 made from carbon fiber 116 are stronger than traditional conductors. Moreover, conductors 110 made from carbon fiber 116 can be made with a smaller over-all cross section and perform with the same electrical resistance traditional conductors. For example, in the case of carbon fibers 116 each conductor 110 is about 4 microns or larger in diameter and has thousands of very flexible individual conductors. Meaning that the overall conductor itself can be of much smaller diameter, resulting in less of an obstruction to blood flow when implanted via a vessel, vein, or artery. The smaller diameter with superior performance also allows for the development and implantation of devices into organs and other locations not currently possible. The smaller diameter of the devices also allows for the implantation of multiple neuro-sensing and neuro-stimulation devices without discomfort to the patient.

Carbon fiber is also diamagnetic in nature making it ideally suited for use in conductors for implanted medical devices that are exposed to MRI, and MRT electromagnetic induction along with other electromagnetic interference fields present in our complex modern environment. The design of future MRI machines is stated to be 17.5 Tesla and much higher frequency. The use of self-resonance, and notch filter devices that are tuned for the current technology may overheat when exposed to other frequencies outside the notch filter narrow range, and will not be compatible with the next generation of NRI technology. Conductors 110 formed from carbon fiber and/or nano-tube carbon fiber, however, will not be faced with the same challenges in being compatible with a variety of frequencies, such as 17.5 Tesla and above.

As shown in FIG. 6, each electrical conductor 110 includes a conductive distal tip 120 electrically connected to a respective one of electrode rings 108. The tip 120 of the conductor can be made of the same material as the other electrode bands, e.g., bismuth, pyrolytic graphite, or HOPG. In accordance with some embodiments, the tip of the conductor 120 can simply include bundle of fibers 116 forming each conductor 110 (without dielectric insulation material 114), or the bundle of fibers 116 the tip 120 can include a crimped ferrule around the outer perimeter of the bundle, thereby forming the tip 120. In the embodiment of FIG. 6, tip 120 is shown with a ferrule crimped around the bundle of fibers 116 extending out of dielectric insulation material 114. The tip 120 (whether that includes just the bundle of fibers 116 alone or whether it includes the ferrule crimped around the bundle of fibers 116) is then mechanically and electrically connected/bonded to its respective electrode ring 108 with a composite adhesive material 118, described in more detail below. The crimped ferrule can be made from bismuth, and/or a conductive composite material which is made of diamagnetic micro particulates in high concentrations.

As shown in FIG. 7, composite adhesive material 118 is used to secure conductive distal tip 120 of each electrical conductor 110 to a respective electrode ring 108, thereby electrically coupling fibers 116 for a given conductor 110 with one of electrode rings 108. One complexity in using pyrolytic graphite or HOPG to form electrode rings 108 is the connection to other devices, e.g. carbon fibers and/or nano-tube carbon fibers 116. Composite adhesive material 118 includes a micro-particle concentration of carbon fiber and/or pyrolytic graphite powders. The micro-particle concentration of nanometer and micron size carbon fiber and/or pyrolytic graphite powders in a mixture with adhesives bond well with the pyrolytic graphite or HOPG being used to form electrode rings 108. These nanometer and micron size carbon fiber and pyrolytic graphite particles make a conductive bond between the pyrolytic graphite (or HOPG) electrode rings 108 and fibers 116 of conductor 110, forming an electrical connection between conductive distal tip 120 of conductor 110 and electrode rings 108. In some embodiments, adhesive 118 includes a two-part epoxy, cyanoacrylate, and/or UV cured adhesives, including UV cured cyanoacrylate. Adhesive 118 can be applied in a viscous form and then cured. The percentage of concentration of the nanometer and micron size carbon fiber and or pyrolytic graphite powers can be adjusted to optimize the lowest resistance and an acceptable bond strength of the joint. These adhesives have been shown to be biocompatible.

Moreover, using conductors 110 formed from carbon fiber and/or nano-tube carbon fiber presents the possibility of ingress of water of other body fluids into the interior of the carbon fiber or nano tube carbon fiber conductor 110, fore example, at the termination of dielectric insulation material 114. The above described adhesive helps to avoid this issue. Moreover, embodiments of the present invention ensure that during the connection of conductor 110 to electrode ring 108 or other device the concentrated nanometer/micron carbon fiber or pyrolytic graphite adhesive is also made to flow over the extremities and partially into the interior of dielectric insulation material 114, thereby sealing the interior of the conductor. This is achieved by technique in the process or by application of a vacuum to the proximal end of the carbon fiber conductor 110 during the process of connecting conductive distal tip 120 of conductor 110 to the electrode to draw adhesive 118 into an interior of dielectric insulation material 114 and between fibers 116. Care is taken to limit the distance the adhesive penetrates conductor 110 (e.g. by setting the vacuum level) as it will stiffen conductor 110 potentially slightly alter the electrical resistance of the same.

Figure 8:
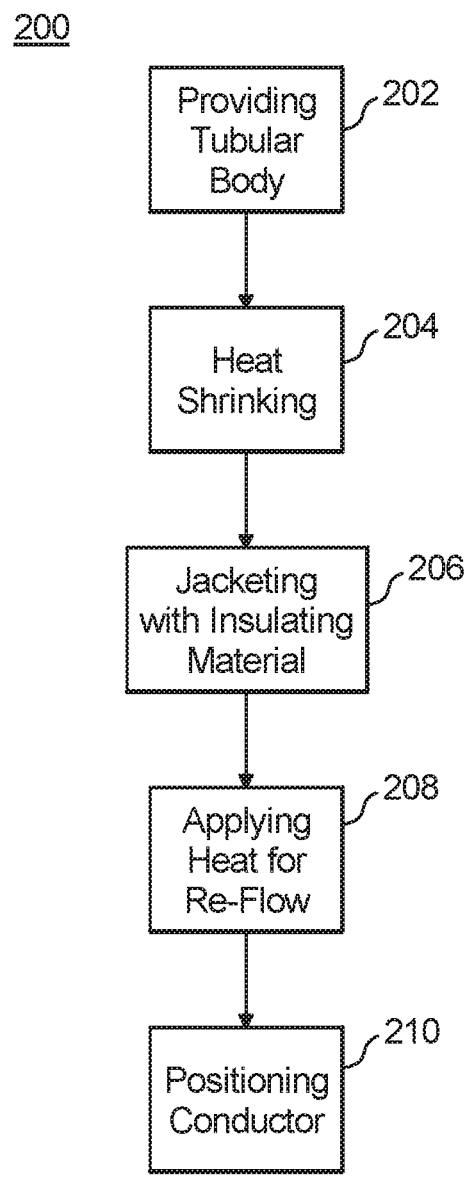
FIG. 8 is a schematic block diagram showing an embodiment of a method for assembling an implantable medical device in accordance with the present disclosure.

Another complexity in using bismuth wires, carbon fibers and/or nano-tube carbon fibers 116 as the conductive material in conductors 110 is applying a dielectric insulation material 114 over bismuth wire, carbon fibers and/or nano-tube carbon fibers 116. As shown in FIG. 8, a method 200 for assembling an implantable medical device having electrical conductors, e.g. electrical conductors 110, includes providing an elongated tubular body, e.g. elongated tubular body 101, having opposed proximal and distal end portions, e.g. proximal end portion 102 and distal end portion 104, as shown schematically by box 202. Method 200 includes heat-shrinking an axially extending bundle of fibers, e.g. fibers 116, with a heat shrink material, e.g. heat shrink material 121, as shown schematically by box 204. Fibers can be formed from bismuth, carbon and/or nano-tube carbon. Heat-shrinking includes compressing the heat shrink material around the axially extending bundle of fibers by heating the heat shrink material. It is shown in U.S. Pat. No. 9,520,213 that the electrical resistance of the carbon fiber conductor will increase if the dielectric insulating jacket material penetrates into and in between the structure of the carbon fibers 116. By heat shrinking around the fibers to tightly compress to the carbon fibers before applying the insulation jacketing and heating the insulation jacketing, penetration into and in-between the structure of the carbon fibers or bismuth can be avoided and the very low resistance characteristics can be maintained as the outer insulation jacket is heated. Method 200 includes jacketing a dielectric insulating material around the axially extending bundle of fibers to form an electrical conductor, as shown schematically by box 206, after heat-shrinking the fibers but before heating the insulating material. The method 200 includes applying heat to the dielectric insulating material, as shown schematically by box 208. The method includes positioning the electrical conductor within the interior lumen of the elongated tubular body, as shown schematically by box 210.

Figure 9:
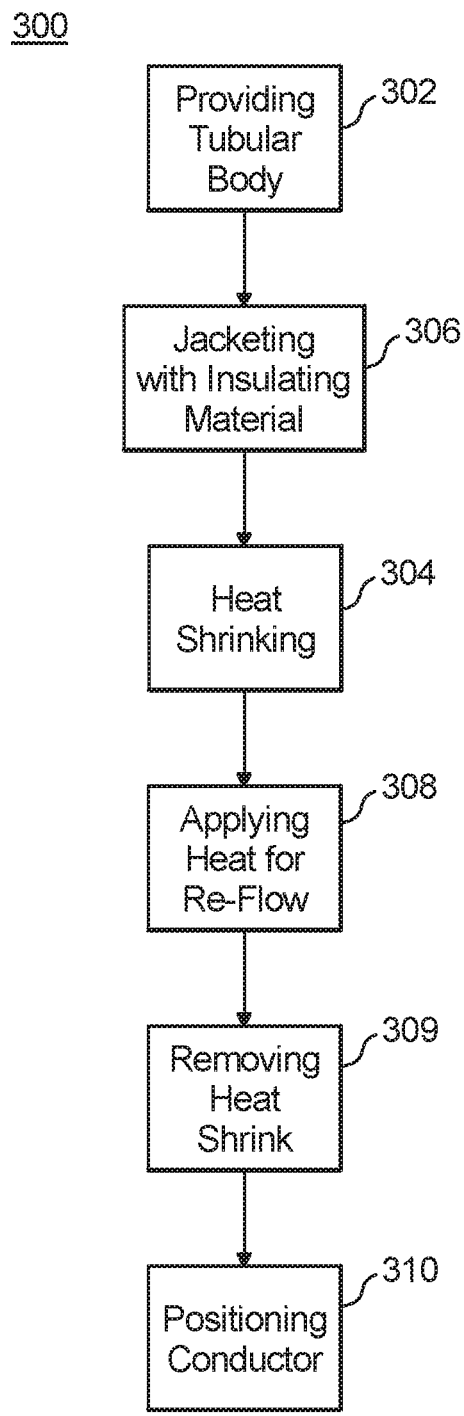
FIG. 9 is a schematic block diagram showing another embodiment of a method for assembling an implantable medical device in accordance with the present disclosure.

As shown in FIG. 9, in some embodiments, a method 300 (similar to 200, except for the changes described below), includes jacketing the dielectric insulating material around the axially extending bundle of fibers, indicated schematically by box 306, before heat-shrinking the axially extending bundle of fibers with the heat shrink material, as indicated schematically by box 304. In other words, heat-shrinking the axially extending bundle of fibers with the heat shrink material includes heat-shrinking over the dielectric insulating material and the axially extending bundle of fibers at the same time with the same heat-shrink material. Meaning that, instead of having heat shrink material 121 directly around the fibers 116, as shown in FIGS. 4B-5, sleeve 114 would be positioned around fibers 116 shown in FIG. 4 directly, and then a layer of heat shrink material, e.g. heat shrink material 121 would be positioned around the outer circumference of sleeve 114 and, indirectly, also over the bundle of fibers.

With continued reference to FIG. 9, heat-shrinking includes compressing the heat shrink material around the axially extending bundle of fibers and the dielectric insulation by heating the heat shrink material. The insulation jacket is then reflowed (e.g. heated and melted) by means of exposing it to a heat reflow process, as indicated schematically by box 308. The application of the heat and time can be adjusted to produce good quality insulated conductors. In this embodiment, method 300 includes removing the heat shrink material after applying heat to the dielectric insulating material leaving only the high dielectric material fully encasing the carbon fibers, as indicated schematically by box 309. In other words, the final conductor resulting from the method of FIG. 9 will be similar to that shown in FIG. 5, except without heat shrink layer 121.

Method 300 includes positioning the electrical conductor within the interior lumen of the elongated tubular body, as shown schematically by box 310. In either method 200 or 300, it is also contemplated that the conductors with an initial dielectric insulating layer can then be extruded over, jacketed over, and/or reflowed with additional dielectric insulation sufficient for the defibrillation circuit conductors. Defibrillation conductors typically require a much higher insulation voltage high potential (Hi-Pot) test. The higher insulation is achieved by better dielectric materials and by increasing the wall thickness of the dielectric materials over the high voltage conductors. The conductors can be double jacketed to improve the high voltage performance. A second reflow is utilized over the entire assembly of multiple conductors and electrode assembly. This reflow seals the entire assembly hermetically. When manufactured in accordance with embodiments of the present invention, it is possible to produce implantable electrical devices, leads, and neuro-sensing and neuro-stimulation devices that have lower impedance, are diamagnetic and have greater immunity to external electromagnetic induction fields.

Moreover, the harmful effects of the ionizing radiation utilized in fluoroscopy is causing some interventional procedures to be moved from fluoroscopy imaging to MRI imaging crating a need for more MRI compatible and MRI safe deflectable catheters used in various procedures. These catheters can also benefit from the use of diamagnetic materials such as is described above with the addition of the use of carbon fiber in the construction of the braid, the pull wires, the pull anchor ring, and the marker bands. The use of carbon fiber for the pull wires is advantageous as the carbon fiber is stronger than steel, can be made in a smaller diameter for the same application and has the added advantage of not being able to push, only pull preventing a puncture to the vessel in the event of failure of the device. The use of the above described diamagnetic materials and methods allow for the design and manufacture a wide array of MRI compatible intervention devices. This can prevent the harmful exposure to the ionizing radiation of fluoroscopy, saving the lives of those in the health care complex electromagnetic environment.

The use of the above described diamagnetic materials for conductors and contacts also has advantages in the aerospace environment. The use of diamagnetic conductors lowers the radar reflection, and the use of carbon fiber or nano tube carbon fiber conductors lowers the weight of the conductor, or bundles of conductors as used in aircraft. These conductors also reduce cross talk interference between conductors. As the conductors have lower resistance, they also lower the heat generated in the flow of energy through them. They also have uses in space as the carbon fiber and nano tube carbon fiber conductors are able to handle extreme temperatures and also resist the harsh radiation of space, being of smaller cross section, lighter weight, lower resistance, and very durable.

The methods and systems of the present disclosure, as described above and shown in the drawings, provide for implantable medical devices, such as heart leads, neuro-sensing and neuro-stimulation devices, and intervention catheters and devices, constructed from diamagnetic materials to reduce the adverse effects of applied external electromagnetic induction into the millivolt signals and prevents the heating of the devices and the surrounding tissue. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. An implantable medical device comprising:
   a) an elongated tubular body having opposed proximal and distal end portions and defining a longitudinal axis, the elongated tubular body including an interior lumen extending therethrough;
   b) a plurality of axially spaced apart electrode rings operatively associated with the distal end portion of the tubular body, wherein the electrode rings are formed from at least one of bismuth or pyrolytic graphite; and
   c) a plurality of electrical conductors extending through the interior lumen of the tubular body, wherein each of the electrical conductors is operatively associated with a respective one of the plurality of electrode rings, wherein the electrical conductors are formed from at least one of bismuth or carbon fiber, and each electrical conductor comprises a composite adhesive material that secures the respective electrical conductor to a respective one of the plurality of electrode rings, the composite adhesive material including a micro-particle concentration of at least one of carbon fiber powder or pyrolytic graphite powder.

2. An implantable medical device as recited in claim 1, further comprising an inner dielectric support structure extending through the interior lumen of the elongated tubular body for supporting the plurality of electrical conductors, wherein the inner dielectric support structure is positioned radially inward from the electrode rings.

3. An implantable medical device as recited in claim 1, further comprising a dielectric insulator ring positioned between axially adjacent pairs of spaced apart electrode rings.

4. An implantable medical device as recited in claim 1, wherein each of the electrical conductors is comprised of an axially extending bundle of fibers, and wherein each axially extending bundle of fibers further comprises a jacket of dielectric insulation material.

5. An implantable medical device as recited in claim 1, wherein each of the electrical conductors includes a conductive distal tip electrically connected to a respective one of the plurality of electrode rings.

6. An implantable medical device as recited in claim 1, further comprising a connector assembly operatively associated with the proximal end portion of the tubular body for connecting the implantable medical device to an implantable stimulation device.

7. An implantable medical device as recited in claim 1, wherein the electrical conductor is a carbon fiber, and the carbon fiber is a nano-tube carbon fiber.

8. An implantable medical device as recited in claim 1, wherein the micro-particle concentration of at least one of carbon fiber powder or pyrolytic graphite powder comprises a mixture of both carbon fiber powder and pyrolytic graphite powder, and an adhesive.

9. An implantable medical device as recited in claim 8, wherein the adhesive includes at least one of a two-part epoxy, cyanoacrylate, or ultra-violet cured adhesives.

10. An implantable medical device as recited in claim 1, wherein the electrode rings are co-axial with one another.

* * * * *